United States Patent [19]
Jiles et al.

[11] Patent Number: 6,084,404
[45] Date of Patent: Jul. 4, 2000

[54] APPARATUS AND METHOD FOR ON-LINE BARKHAUSEN MEASUREMENT

[75] Inventors: David C. Jiles, Ames, Iowa; Anthony Parakka, Plano, Tex.

[73] Assignee: Iowa State University Research Foundation, Inc., Ames, Iowa

[21] Appl. No.: 09/036,533

[22] Filed: Mar. 6, 1998

[51] Int. Cl.[7] .......................... G01N 27/72; G01N 27/82; G01R 33/12

[52] U.S. Cl. .......................... 324/232; 324/209; 324/239; 324/240

[58] Field of Search .................................. 324/206, 209, 324/223, 228, 232, 239–243

[56] References Cited

U.S. PATENT DOCUMENTS

| | | | |
|---|---|---|---|
| 2,065,119 | 12/1936 | Davis, Jr. | 324/240 X |
| 4,827,215 | 5/1989 | van der Walt | 324/232 X |
| 5,619,135 | 4/1997 | Kohn et al. | 324/209 X |

FOREIGN PATENT DOCUMENTS

| | | | |
|---|---|---|---|
| 696369 | 11/1979 | U.S.S.R. | 324/232 |
| 2031155 | 4/1980 | United Kingdom | 324/232 |

OTHER PUBLICATIONS

Kivimaa, et al; "Influence of Tensile Stress in Steel Cables on Magnetic Barkhausen Noise", IEEE Transactions on Magnetics 29, No. 6 Nov. 1993.

Review of Magnetic Methods for Nondestructive Evaluation; NDT International, vol. 21, No. 5, Oct., 1988, pp. 311–319; D.C. Jiles.

*Primary Examiner*—Gerard Strecker

[57] ABSTRACT

Apparatus and method for measuring the Barkhausen signal of a moving magnetic film, ribbon or fiber wherein first and second stationary electromagnet coils are arranged and separated by a distance, d, along the path of movement of the film, ribbon or fiber. The first and second coils are energized in a manner to generate first and second opposing DC magnetic fields through which the moving film, ribbon or fiber passes along its path of movement. As the film, ribbon or fiber moves through the first and second opposing magnetic fields at a velocity, v, it experiences one complete cycle of magnetization in a period of time equal to d/v. A stationary third signal pick-up coil is disposed between the first and second coils to detect the Barkhausen signal from the moving film, ribbon or fiber. The pick-up coil typically is disposed midway between the first and second coils where the Barkhausen signal will be approximately maximum.

6 Claims, 1 Drawing Sheet

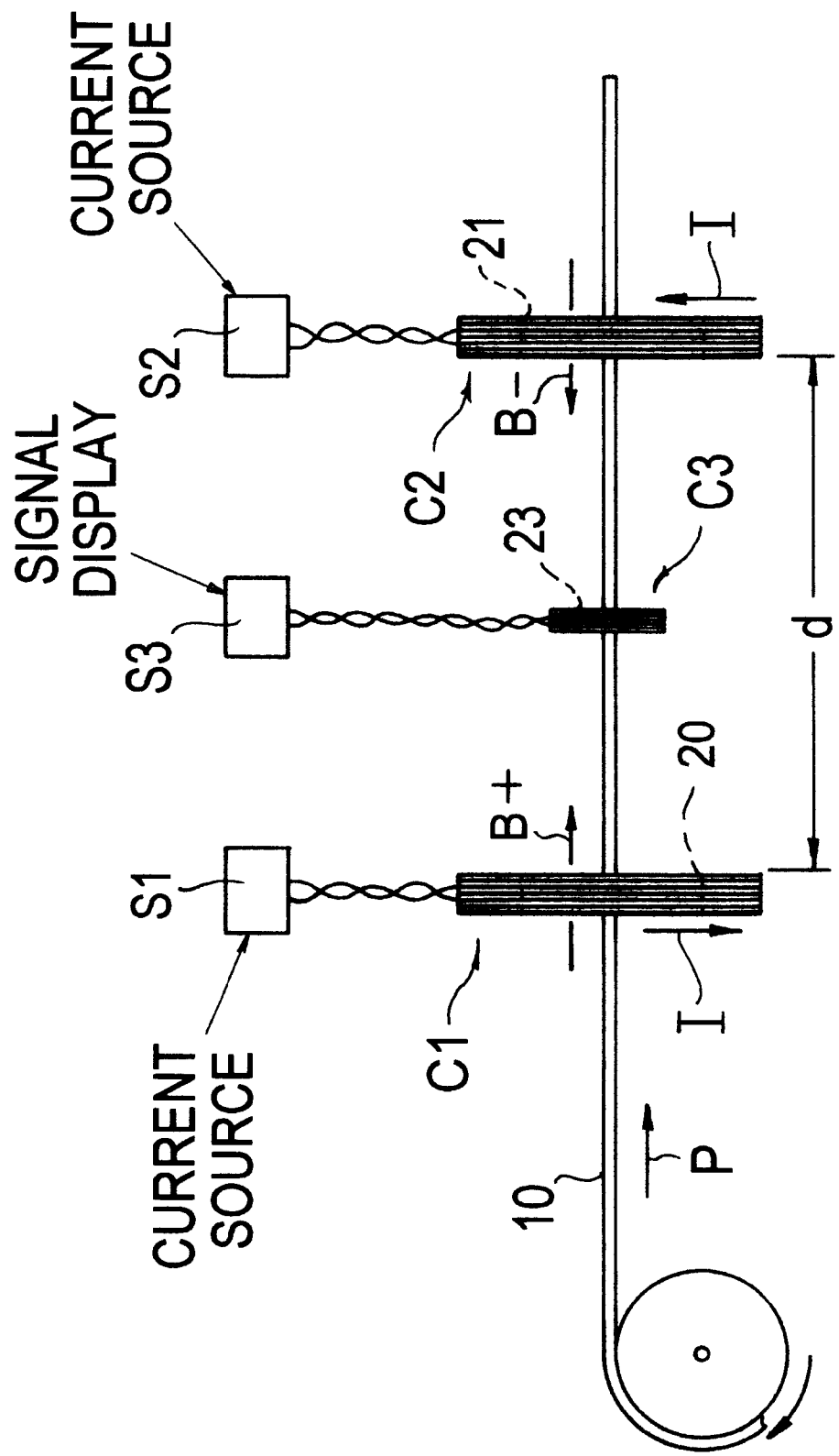

APPARATUS AND METHOD FOR ON-LINE BARKHAUSEN MEASUREMENT

FIELD OF THE INVENTION

The present invention relates to measurement of a micromagnetic signal, particularly the Barkhausen signal, of a moving magnetic film, ribbon or fiber.

BACKGROUND OF THE INVENTION

The micromagnetic Barkhausen signal is a parameter that is not measured in the production of amorphous magnetic films, ribbons, or fibers, and yet it can be useful in evaluating magnetic films, ribbons, or fibers since the signal depends on the differential permeability and is representative of the hysteresis curve of the material. The Barkhausen signal is described in detail by Jiles in the technical article entitled "Review of Magnetic Methods for Nondestructive Evaluation", NDT International, 21, 311, 1988, the teachings of which are incorporated herein by reference.

Micromagnetic Barkhausen measurements should be made when the average magnetization of the magnetic material changes from one direction to another. This indicates that the material should be close to its coercive point. Measurement of the micromagnetic Barkhausen signal thus requires a change in the magnetic field which can be accomplished by the spatial magnetic field gradient experienced by a given portion of the magnetic specimen as it moves through a coil. In the past, the Barkhausen signal has been measured with a stationary specimen which is subjected to a time varying magnetic field. However, when the specimen happens to be in motion, such as occurs during production of magnetic film, ribbon, or fiber, use of a time varying field to make such a Barkhausen signal measurement would involve complex synchronization of the position of a given portion of the specimen with the time varying field strength.

An object of the present invention is to provide a simple apparatus and method for measuring a Barkhausen or other signal of a moving film, ribbon, fiber or other magnetic material without the need for complex synchronization of the position of a given portion of the specimen with a time varying magnetic field.

Another object of the present invention is to provide apparatus and method for measuring a Barkhausen, or other signal, of a moving film, ribbon, fiber or other magnetic material, wherein components of the measuring apparatus are disposed stationary while the magnetic film, ribbon, or fiber is moving.

SUMMARY OF THE INVENTION

One embodiment of the present invention provides apparatus and method for measuring a signal, such as for example the Barkhausen signal, of a moving magnetic film, ribbon, fiber or other magnetic material or member, wherein first and second stationary electromagnetic field generating coils are arranged and separated by a distance, d, along the path of movement of the magnetic material. The first and second coils are energized in a manner to generate first and second opposing components of the magnetic field through which the moving magnetic material passes along its path of movement. As the magnetic material moves through the total magnetic field generated by the coils at a velocity, v, it experiences one half cycle of magnetization in a period of time equal to d/v. A stationary third signal pick-up coil is disposed between the first and second coils to detect the signal from the moving magnetic material. Preferably, the pick-up coil is disposed midway between the first and second coils where the Barkhausen signal will be approximately maximum because the spatial gradient of the magnetic field is a maximum at that location.

The present invention thereby provides for measurement of the Barkhausen signal of a moving magnetic film, ribbon, fiber, or other magnetic material using a simple arrangement of stationary coils relative to which the magnetic material moves. All of this is thereby achieved without the need for complex synchronization of the position of a given portion of the specimen with a time varying magnetic field strength.

DESCRIPTION OF THE DRAWING

The FIGURE is a schematic view of apparatus in accordance with an embodiment of the present invention for measuring the Barkhausen signal of a moving magnetic film, ribbon, fiber or other magnetic material using an arrangement of stationary coils.

DETAILED DESCRIPTION OF THE INVENTION

Referring to the FIGURE, apparatus in accordance with an embodiment of the present invention is schematically illustrated for measuring the Barkhausen signal of a moving magnetic film, ribbon, fiber, or other elongated magnetic material or member 10. The film, ribbon or fiber 10 can be moved by ejection from a spinning wheel during high volume manufacture of the magnetic film, ribbon or fiber. For subsequent "off line" evaluation, the magnetic film, ribbon or fiber can be attached to a Plexiglass or other support plate which is moved relative to electromagnet coils as explained below.

The apparatus comprises first and second stationary, circumferentially wound, annular electromagnet coils C1, C2 that are disposed along the length of the path P of movement of the film, ribbon or fiber 10. The first and second coils are spaced apart by a distance, d, as shown in the FIGURE along the path P. The first and second coils C1, C2 are energized by respective DC electrical current sources S1 and S2 in a manner to generate first and second opposing DC magnetic fields B+, B− as shown (current I flows in opposite directions around those two coils as illustrated by arrows) through which the moving film, ribbon or fiber passes along its path P of movement as shown in the FIGURE.

The first and second coils C1, C2 typically can comprise a few hundred (e.g. 200–400) circumferential turns of copper wire carrying an electrical current of a few amperes. The first and second coils C1, C2 form annular coils with inner bores 20, 21 through which the moving film, ribbon or fiber 10 passes. The coils C1, C2 can have an inner bore diameter of 3–12 inches when the moving film or ribbon has a width of 0.25–6 inches and thickness of 1–2 inches. The coils C1, C2 can be spaced 3–12 inches apart along path P. The magnetic fields B+, B− should have equal magnitudes oriented in opposite directions. The field amplitude at the center of the repsective coils is typically 500–2000 Amperes/meter.

As the film, ribbon or fiber moves through the first and second opposing magnetic fields B+, B− at a velocity, v, it experiences one half cycle of magnetization (change in direction of magnetization) in a period of time equal of d/v seconds as a result of the presence of the opposing magnetic fields B+, B−. A stationary third signal pick-up wire coil C3 is disposed between the first and second coils C1, C2 to detect the Barkhausen signal generated by the moving film, ribbon or fiber as a result of the change of magnetization of the magnetic film, ribbon or fiber 10 from one direction to another. The coil C3 is connected by wires to a signal display S3, such as an oscilloscope. Since the Barkhausen signal is approximately maximum at the midpoint (equidistant) between the coils C1, C2, the pick-up coil C3 preferably is disposed midway between the C1, C2 as shown in the FIGURE.

The pick-up coil C3 typically can comprise a circumferentially wound coil comprising 10–100 turns of copper wire having an inner bore 23 with an inner bore coil diameter of 1–3 inches when the coils C1, C2 are dimensioned as described above and generate magnetic fields B+, B− of the magnitude described above. The pick-up coil C3 forms an annulus through which the moving film, ribbon or fiber 10 passes. The pick-up coil C3 is connected to an oscilloscope to indicate the measured Barkhausen micromagnetic signal from the moving film, ribbon or fiber 10.

The present invention thereby provides apparatus and method for measurement of the Barkhausen signal of a moving magnetic material consisting of a film, ribbon or fiber using a simple arrangement of stationary coils relative to which the magnetic film, ribbon or fiber moves without the need for complex synchronization of the position of a given portion of the film or ribbon 10 with a varying field strength. The present invention thereby provides apparatus and method for the on-line, non-destructive measurement of the Barkhausen signal (e.g. while the magnetic film, ribbon or fiber is moving during production to provide a non-destructive magnetic test signal useful for assessment of quality of the magnetic film, ribbon or fiber). The present invention can be practiced with a stationary magnetic film and moving coils so as to provide relative movement between the material and first and second opposing magnetic fields to generate a Barkhausen signal picked up by a third pick-up coil also stationary relative to the first and second coils.

Although the present invention has been described in terms of a specific embodiment thereof, it is not intended to be limited thereto but rather only as set forth in the appended claims.

What is claimed is:

1. Apparatus for measuring a signal from a moving magnetic material comprising first and second electromagnet coil means for generating opposing magnetic fields, said first and second coil means being disposed and separated by a distance along a path of relative movement between the material and said opposing magnetic fields so as to subject said material to magnetization that generates a Barkhausen signal, and a third signal pick-up means disposed between the first and second coil means to detect the signal from the material.

2. Apparatus for measuring a signal from a moving magnetic elongated material comprising first and second stationary electromagnet coils disposed and separated by a distance, d, along a path of movement of the elongated material moving at a velocity, v, relative to said coils, direct current means for energizing said first coil and said second coil to generate first and second opposing DC magnetic fields through which said moving elongated material passes along its path of movement so as to be subjected to a half cycle of magnetization in a period of time equal to d/v, and a stationary third signal pick-up coil disposed between the first and second coils to detect a signal from the moving elongated material.

3. The apparatus of claim 2, wherein said pick-up coil is disposed midway between the first and second coils where the signal will be approximately maximum.

4. The method of claim 1, wherein said moving magnetic material is moved as a result of ejection from a spinning wheel or driver.

5. A method for measuring a signal from a moving magnetic material comprising the steps of generating opposing magnetic fields by stationary field generating means separated by a distance, d, along a path of movement of the magnetic material, moving said material at a velocity, v, through said opposing magnetic fields so as to subject said material to a half cycle of magnetization in a period of time equal to d/v, and detecting the signal from the moving material.

6. The method of claim 5 where the signal is detected midway between first and second stationary field generating means.

* * * * *